United States Patent
Convents et al.

(10) Patent No.: US 6,489,279 B2
(45) Date of Patent: *Dec. 3, 2002

(54) LAUNDRY AND CLEANING COMPOSITIONS CONTAINING XYLOGLUCANASE ENZYMES

(75) Inventors: Andre Christian Convents, Cincinnati, OH (US); Rosa Laura Moese, West Chester, OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/235,594

(22) Filed: Jan. 22, 1999

(65) Prior Publication Data

US 2001/0014659 A1 Aug. 16, 2001

(51) Int. Cl.$^7$ .............. C11D 1/14; C11D 3/386; C11D 3/395

(52) U.S. Cl. ............. 510/226; 510/308; 510/309; 510/310; 510/392; 510/393; 510/530; 134/25.2; 8/137; 8/111; 435/209

(58) Field of Search .......... 435/209; 510/392, 510/393, 226, 530, 308, 309, 310; 8/137, 401; 134/42, 25.2

(56) References Cited

U.S. PATENT DOCUMENTS

| | | | | |
|---|---|---|---|---|
| 5,356,803 A | | 10/1994 | Carpenter et al. ......... 435/200 |
| 5,723,328 A | * | 3/1998 | Dalboege et al. .......... 435/209 |
| 5,767,364 A | | 6/1998 | de Silvia et al. .......... 800/205 |
| 5,821,398 A | | 10/1998 | Speirs et al. ............ 800/205 |
| 5,840,550 A | | 11/1998 | Nishitani et al. ........... 435/97 |
| 5,872,091 A | * | 2/1999 | Cuperus et al. ........... 510/300 |

FOREIGN PATENT DOCUMENTS

| | | | | |
|---|---|---|---|---|
| JP | 07059565 A | 3/1995 | | |
| WO | WO 93/17101 | 9/1993 | ............ | C12N/9/24 |
| WO | WO 93/20193 | 10/1993 | ............ | C12N/9/42 |
| WO | WO 94/13797 | 6/1994 | ............ | C12N/15/11 |
| WO | 94/14953 | * 7/1994 | | |
| WO | WO 94/26880 | 11/1994 | ............ | C12N/9/24 |
| WO | 96/11262 | * 4/1996 | | |
| WO | 96/19570 | * 6/1996 | | |
| WO | WO 97/13862 | 4/1997 | ............ | C12N/15/56 |
| WO | WO 98/28991 | 7/1998 | ............ | A23L/2/02 |
| WO | 98/50513 | * 11/1998 | | |

OTHER PUBLICATIONS

T. Matsumoto, F. Sakai, T. Hayashi *A xyloglucan–specific endo–1–4–.beta.–glucanase isolated from auxin–treated pea stems*; Plant Physiol. (1997), 114(2), 661–667 (Oct. 1997).

A. Tabuchi, S. Kamisaka, T. Hoson, *Purification of xyloglucan hydrolase/endotransferase from cell walls of azuki bean epicotyls*; Plant Cell Physiol. (1997), 38(6), 653–658 (Aug. 1997).

A. Rejon–Palomares, J. M. Garcia–Garrido, J. A. Ocampo, I. Garcia–Romera, *Presence of xyloglucan–hydrolyzing glucanases (xyloglucanases) in arbuscular mycorrhizal symbiosis*; Symbiosis (1996), 21(3), 249–261 (May 1996).

T. Matsumoto, T. Takeda, F. Sakai, T. Hayashi, *Purification of xyloglucanases from auxin–treated pea stems*; Wood Res. (1996), 83, 21–22 (Aug. 1996).

G. Maclachlan, C. Brady, *Endo–1,4–.beta.glucanase, xyloglucanase, and xyloglucan endo–transglycocylase activities versus potential substrates in ripening tomatoes*; Plant Physiol. (1994), 105(3), 965–74 (Feb. 1994).

J. de Silva, C. D. Jarman, D. A. Arrowsmith, M. S. Stronach, S. Chengappa, C. Sidebottom, J. S. Reid, *Molecular characteization of a xyloglucan–specific endo–(1.fwdarw.4)–.beta.–D–glucanase(xyloglucan endo–transglycosylase) from naturtium seeds*; Plant J. (1993), 3(5), 701–11 (Jan. 1993).

J. Acebes, I. Zarra, *Cell wall glycanases and their activity against the hemicelluloses from pine hypocotyls*; Physiol. Plant.(1992), 86(3), 433–8 (Mar. 1992).

V. Farkas, Z. Sulova, E. Stratilova, R. Hanna, G. Maclachlan *Cleavage of xyloglucan by nasturtium seed xyloglucanase and transglycosylation to xyloglucan subunit oligosaccharides*; Arch. Biochem. Biophys. (1992), 198(2), 365–70 (Apr. 1992).

G. Maclachlan, C. Brady *Multiple forms of 1,4–.beta.–glucanase in ripening tomato fruits include a xyloglucanase activatable by xyloglucan oligosaccharides* Aust. J. Plant Physiol. (1992), 19(2), 137–46 (Mar. 1992).

Y. Kato, K. Matsuda *Occurence of a soluble and low molecular weight xyloglucan and its origin in etiolated mung bean hypocotyls*; Agric. Biol. Chem. (1981), 45(1), 1–8 (Nov. 1981).

J. Vincken, L. van den Broek, D. van der Lei, G. Beldman, A. Voragen *Fungal and plant xyloglucanases may act in concert during liquefaction of apples*; J. Sci. Food Agric. (1997), 73(4) 407–416 (Mar. 1997).

* cited by examiner

Primary Examiner—Gregory Delcotto
(74) Attorney, Agent, or Firm—C. Brant Cook; Kim W. Zerby; Steven W. Miller

(57) ABSTRACT

Laundry or cleaning products comprising one or more enzymes exhibiting endoglucanase activity specific for xyloglucan, and methods for laundering fabrics and cleaning dishes and tableware with aqueous solutions containing an effective amount of one or more enzymes exhibiting endoglucanase activity specific for xyloglucan.

10 Claims, No Drawings

LAUNDRY AND CLEANING COMPOSITIONS CONTAINING XYLOGLUCANASE ENZYMES

RELATED APPLICATION

This application claims priority under 35 U.S.C. §119 to International Application Ser. No. PCT/US98/09126, filed May. 5, 1998.

TECHNICAL FIELD

The present invention relates to laundry and cleaning compositions comprising enzymes with xyloglucanase activity.

BACKGROUND OF THE INVENTION

As previously described in WO 94/14953, published Jul. 7, 1994 by Novo Nordisk, endoglucanases (EC no. 3.2.1.4) constitute a group of hydrolases which catalyze endo hydrolysis of 1,4-β-D-glycosidic linkages in cellulose, cellulose derivatives (such as carboxy methyl cellulose and hydroxy ethyl cellulose), lichenin, β-1,4 bonds in mixed β-1,3 glucans (such as cereal β-D-glucans or xyloglucans) and other plant material containing cellulosic parts. The authorized name is endo-1,4-β-D-glucan 4-glucano hydrolase, but the abbreviated term endoglucanase is also used.

Endoglucanases have been found to be produced by various types of organisms such as plants and microorganisms, and endoglucanases of a wide variety of specificities are said to have been identified. For instance, xyloglucan specific endoglucanases have been identified in various plants, see for example, the disclosure of Fry et al., Biochem. J. (1992), Vol 282, pp 821–828, Nishitani and Tominaga, The Journal of Biol. Chemistry (1992). Vol. 267, No. 29, pp. 21058–21064, Hayashi et al., Plant Physiol., (1984), Vol. 75, pp. 605–610, McDougall and Fry, J. Plant Physiol., (1991), Vol. 137, pp. 332–336, and WO 93/17101. All of these enzymes have been found to have transferase activity (as defined e.g. by Fry et al., 1992 and Nishitani et al., 1992) and are therefore said not to be classified as a real endoglucanase. Further, a xyloglucan specific endoglucanases in microorganisms is described in WO 94/14953. Therein, it is generally stated that "endoglucanases having a high xyloglucan-degrading activity may be of particular use for degradations of cell wall material having a high xyloglucan content, for instance in the wine and fruit industry, for pectin-extraction and for removal of hemicelluloses from textile fibres". Specifically referred to for this last property is the use of these enzymes to manufacture textile fibers:

"The hemicellulose like xyloglucan has to be removed from plant fibers like cotton, flax, hemp and jute before these can be used for textiles. For this purpose endoglucanase of type II [i.e., the xyloglucan-specific enzymes] has the advantage that it specifically removes the xyloglucan without damaging the cellulose. This endoglucanase may be used alone or together with other enzymes (e.g. pectinases) active on the pectic substances on the fibers."

"Furthermore, the endoglucanases of the invention and analogous thereof may be used to treat cellulose fibres or cellulose-fibre rich material. The endoglucanases may e.g. be used in the paper industry to improve the drainage of pulp, and to treat fabrics such as cotton fabrics, to give a more smooth fabric." [At page 12.]

An object of the invention is to provide laundry and cleaning compositions containing enzymes with a specified level of xyloglucanase activity. These and other objects will be apparent from the detailed description herein.

BACKGROUND DOCUMENTS

See: Fry et al., Biochem. J. (1992), Vol. 282, pp 821–828, Nishitani and Tominaga, The Journal of Biol. Chemistry (1992). Vol. 267, No. 29, pp. 21058–21064, Hayashi et al., Plant Physiol., (1984), Vol. 75, pp. 605–610, McDougall and Fry, J. Plant Physiol., (1991), Vol. 137, pp. 332–336, WO 93/17101, and WO 94/14953. See also: US 5,356,803 for use of Type II endoglycosidases (Endo-D, Endo-H, Endo-F and PNGaseF) in laundry and cleaning compositions.

SUMMARY OF THE INVENTION

The present invention relates to laundry or cleaning products comprising one or more enzymes exhibiting endoglucanase activity specific for xyloglucan, preferably at a level of from about 0.001% to about 1%, more preferably from about 0.01% to about 0.5%, by weight of the composition. The present invention also relates to a method for laundering fabrics (preferably clothes), said method comprising contacting fabrics in need of cleaning with an aqueous solution containing an effective amount of one or more enzymes exhibiting endoglucanase activity specific for xyloglucan, preferably an aqueous solution of a composition according to the present invention. The present invention further relates to a method for cleaning dishes and tableware, said method comprising contacting dishes or tableware in need of cleaning with an aqueous solution containing an effective amount of one or more enzymes exhibiting endoglucanase activity specific for xyloglucan, preferably an aqueous solution of a composition according to the present invention, and more preferably in an automatic dishwashing machine.

As used herein, the term "endoglucanase activity" means the capability of the enzyme to hydrolyze 1,4-β-D-glycosidic linkages present in any cellulosic material, such as cellulose, cellulose derivatives, lichenin, β-D-glucan, or xyloglucan. The endoglucanase activity may be determined in accordance with methods known in the art, examples of which are described in WO 94/14953 and hereinafter. One unit of endoglucanase activity (e.g. CMCU, AVIU, XGU or BGU) is defined as the production of 1 μmol reducing sugar/min from a glucan substrate, the glucan substrate being, e.g., CMC (CMCU), acid swollen Avicell (AVIU), xyloglucan (XGU) or cereal β-glucan (BGU). The reducing sugars are determined as described in WO 94/14953 and hereinafter. The specific activity of an endoglucanase towards a substrate is defined as units/mg of protein.

More specifically, the invention relates to laundry and cleaning compositions comprising an enzyme exhibiting as its highest activity XGU endoglucanase activity (hereinafter "specific for xyloglucan"), which enzyme:

i) is encoded by a DNA sequence comprising or included in at least one of the following partial sequences
(a) ATTCATTTGT GGACAGTGGA C (SEQ ID No: 1)
(b) GTTGATCGCA CATTGAACCA (SEQ ID NO: 2)
(c) ACCCCAGCCG ACCGATTGTC (SEQ ID NO: 3)
(d) CTTCCTTACC TCACCATCAT (SEQ ID NO: 4)
(e) TTAACATCTT TTCACCATGA (SEQ ID NO: 5)
(f) AGCTTTCCCT TCTCTCCCTT (SEQ ID) NO: 6)
(g) GCCACCCTGG CTTCCGCTGC CAGCCTCC (SEQ ID NO: 7)
(h) GACAGTAGCA ATCCAGCATT (SEQ ID NO: 8)
(i) AGCATCAGCC GCTTTGTACA (SEQ ID NO: 9)

(j) CCATGAAGTT CACCGTATTG (SEQ ID NO: 10)
(k) GCACTGCTTC TCTCCCAGGT (SEQ ID NO: 11)
(l) GTGGGCGGCC CCTCAGGCAA (SEQ ID NO: 12)
(m) ACGCTCCTCC AATTTTCTCT (SEQ ID NO: 13)
(n) GGCTGGTAG TAATGAGTCT (SEQ ID NO: 14)
(o) GGCGCAGAGT TTGGCCAGGC (SEQ ID NO: 15)
(p) CAACATCCCC GGTGTTCTGG G (SEQ ID NO: 16)
(q) AAAGATTCAT TTGTGGACAG TGGACGTTGA TCGCACATTG AACCAACCCC AGCCGACCGA TTGTCCTTCC TTACCTCACC ATCATTTAAC ATCTTTCAC CATGAAGCTT TCCCTTCTCT CCCTTGCCAC CCTGGCTTCC GCTGCCAGCC TCCAGCGCCG CACACTTCTG CGGTCAGTGG GATACCGCCA CCGCCGGTGA CTTCACCCTG TACAACGACC TTTGGGGCGA GACGGCCGGC ACCGGCTCCC AGTGCACTGG AGTCGACTCC TACAGCGGCG ACACCATCGC TTGTCACACC AGCAGGTCCT GGTCGGAGTA GCAGCAGCGT CAA- GAGCTAT GCCAACG (SEQ ID NO:17) or
(r) CAGCATCTCC ATTGAGTAAT CACGTTGGTG TTCGGTGGCC CGCCGTGTTG CGTGGCGGAG GCTGCCGGGA GACGGGTGGG GATGGTGGTG GGAGAGAATG TAGGGCGCCG TGTTTCAGTC CCTAGGCAGG ATACCGGAAA ACCGTGTGGT AGGAGGTTTA TAGGTTTCCA GGAGACGCTG TATAGGGGAT AAATGAGATT GAATGGTGGC CACACTCAAA CCAACCAGGT CCTGTACATA CAATGCATAT ACCAATTATA CCTACCAAAA AAAAAAAAAA AAAAAAAAAA AAAA (SEQ ID NO: 18)

or a sequence homologous thereto encoding a polypeptide specific for xyloglucan with endoglucanase activity, ii) is immunologically reactive with an antibody raised against a highly purified endoglucanase encoded by the DNA sequence defined in i) and derived from *Aspergillus aculeatus*, CBS 101.43, and is specific for xyloglucan.

More specifically, as used herein the term "specific for xyloglucan" means that the endoglucanse enzyme exhibits its highest endoglucanase activity on a xyloglucan substrate, and preferably less than 75% activity, more preferably less than 50% activity, most preferably less than about 25% activity, on other cellulose-containing substrates such as carboxymethyl cellulose, cellulose, or other glucans.

Preferably, the specificity of an endoglucanase towards xyloglucan is further defined as a relative activity determined as the release of reducing sugars at optimal conditions obtained by incubation of the enzyme with xyloglucan and the other substrate to be tested, respectively. For instance, the specificity may be defined as the xyloglucan to β-glucan activity (XGU/BGU), xyloglucan to carboxy methyl cellulose activity (XGU/CMCU), or xyloglucan to acid swollen Avicell activity (XGU/AVIU), which is preferably greater than about 50, such as 75, 90 or 100.

The term "derived from" as used herein refers not only to an endoglucanase produced by strain CBS 101.43, but also an endoglucanase encoded by a DNA sequence isolated from strain CBS 101.43 and produced in a host organism transformed with said DNA sequence.

The term "homologue" as used herein indicates a polypeptide encoded by DNA which hybridizes to the same probe as the DNA coding for an endoglucanase enzyme specific for xyloglucan under certain specified conditions (such as presoaking in 5xSSC and prehybridizing for 1 h at −40° C. in a solution of 5xSSC, 5xDenhardt's solution, and 50 µg of denatured sonicated calf thymus DNA, followed by hybridization in the same solution supplemented with 50 µCi 32-P-dCTP labelled probe for 18 h at −40° C. and washing three times in 2xSSC, 0.2% SDS at 40° C. for 30 minutes). More specifically, the term is intended to refer to a DNA sequence which is at least 70% homologous to any of the sequences shown above encoding an endoglucanase specific for xyloglucan, including at least 75%, at least 80%, at least 85%, at least 90% or even at least 95% with any of the sequences shown above. The term is intended to include modifications of any of the DNA sequences shown above, such as nucleotide substitutions which do not give rise to another amino acid sequence of the polypeptide encoded by the sequence, but which correspond to the codon usage of the host organism into which a DNA construct comprising any of the DNA sequences is introduced or nucleotide substitutions which do give rise to a different amino acid sequence and therefore, possibly, a different amino acid sequence and therefore, possibly, a different protein structure which might give rise to an endoglucanase mutant with different properties than the native enzyme. Other examples of possible modifications are insertion of one or more nucleotides into the sequence, addition of one or more nucleotides at either end of the sequence, or deletion of one or more nucleotides at either end or within the sequence.

All parts, percentages and ratios used herein are expressed as percent weight unless otherwise specified. All documents, patents or otherwise, cited herein are, in relevant part or fully, incorporated herein by reference.

DETAILED DESCRIPTION OF THE INVENTION

Endoglucanase specific for xyloglucan have been identified herein as particularly useful for their cleaning properties in laundry and cleaning compositions.

Endoglucanase specific for xyloglucan useful in the present invention preferably is one which has a XGU/BGU, XGU/CMU and/or XGU/AVIU ratio (as defined above) of more than 50, such as 75, 90 or 100.

Furthermore, the endoglucanase specific for xyloglucan is preferably substantially devoid of activity towards β-glucan and/or exhibits at the most 25% such as at the most 10% or about 5%, activity towards carboxymethyl cellulose and/or Avicell when the activity towards xyloglucan is 100%. In addition, endoglucanase specific for xyloglucan of the invention is preferably substantially devoid of transferase activity, an activity which has been observed for most endoglucanases specific for xyloglucan of plant origin.

Endoglucanase specific for xyloglucan may be obtained from the final species *A. aculeatus*, as described in WO 94/14953. Microbial endoglucanases specific for xyloglucan has also been described in WO 94/14953. Endoglucanases specific for xyloglucan from plants have been described, but these enzymes have transferase activity and therefore must be considered inferior to microbial endoglucanses specific for xyloglucan whenever extensive degradation of xyloglucan is desirable. An additional advantage of a microbial enzyme is that it, in general, may be produced in higher amounts in a microbial host, than enzymes of other origins.

An enzyme of the invention may be isolated by a general method involving:

cloning, in suitable vectors, a DNA library from Aspergillus spp., transforming suitable yeast host cells with said vectors, culturing the host cells under suitable conditions to express any enzyme of interest encoded by a clone in the DNA library, and screening for positive clones by determining any endoglucanase activity of the enzyme produced by such clones.

A more detailed description of this screening method is given in WO 94/14953. The DNA sequence coding for the enzyme may for instance be isolated by screening a cDNA library of *Aspergillus aculeatus*, e.g. strain CBS 101.43, publicly available from Centraalbureau voor Schimmelcultures, and selecting for clones expressing enzymes having the ability to hydrolyze β-1,3 and/or β-1,4 bonds between two glucose molecules in polymers containing glucose (e.g. cellulose, cereal β-glucans or xyloglucans). The appropriate DNA sequence may then be isolated from the clone by standard procedures, e.g. as described in WO 94/14953, Example 1. It is expected that a DNA sequence coding for a homologous enzyme may be derived by similarly screening a cDNA library of another microorganism, in particular a fungus, such as a strain of Aspergillus, in particular *A. aculeatus* or *A. niger*, a strain of Trichoderma, in particular *T. harianun, T. reesie*, a strain of Fusarium, in particular *F. oxysporum* or a strain of Humicola.

Alternatively, the DNA coding for an endoglucanase of the invention may, in accordance with well-known procedures, conveniently be isolated from DNA from any of the above mentioned organisms by use of oligonucleotide probes, such as 20mer probes, prepared on the basis of a DNA sequence disclosed herein. For instance, a suitable oligonucleotide probe may, e.g., be prepared on the basis of any of the partial nucleotide sequences a)-p) listed in WO 94/14953.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the endoglucanase specific for xyloglucan should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the endoglucanase, the promoter and the terminator, respectively, and to insert them into suitable vectors are well known to persons skilled in the art (cf, for instance, Sambrook et al., *Molecular Cloning. A Laboratory Manual*, Cold Spring Harbor, N.Y. 1989).

The host cell which is transformed with the DNA sequence encoding the enzyme useful for the present invention compositions is preferably a eukaryotic cell, in particular a fungal cell such as a yeast or filamentous fungal cell. In particular, the cell may belong to a species of Aspergillus, most preferably *Aspergillus oryzae* or *Aspergillus niger*. Fungal cells may be transformed by a process involving protoplast formation and transformation of the protoplasts followed by regeneration of the cell wall in a manner known in the art. The use of Aspergillus as a host microorganism is described in EP 238,023 (of Novo Nordisk A/S). The host cell may also be a yeast cell, e.g. a strain of Saccharomyces, in particular *Saccharomyces cerevisiae*.

The medium used to culture the transformed host cells may be any conventional medium suitable for growing the host cells in question. The expressed endoglucanase specific for xyloglucan may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The thus purified endoglucanase may be employed for immunization of animals for the production of antibodies. More specifically, antiserum against the endoglucanase specific for xyloglucan may be raised by immunizing rabbits (or other rodents) according to the procedure described by N. Axelsen et al. in: *A Manual of Quantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation (($NH_4)_2SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al, Chapter 2).

The endoglucanases specific for xyloglucan useful in the present invention compositions may be produced essentially free from other plant cell wall degrading enzymes. This makes it possible to use the enzymes alone or together with other enzymes, such as galactanases and xylanases, to give the optimal combination of enzymes for a particular application. It is thereby possible to design enzyme combinations, which only degrade specific parts of the plant cell.

The enzyme preparation useful in the present invention compositions may be prepared in accordance with methods known in the art and may be in the form of a liquid or a dry preparation. For instance, the enzyme preparation may be in the form of a granulate or a microgranulate. The enzyme to be included in the preparation may also be stabilized in accordance with methods known in the art.

The enzyme preparation useful in the present compositions may, in addition to an endoglucanase specific for xyloglucan, contain one or more other detergent enzymes and/or other plant cell wall degrading enzymes, for instance those with cellulytic, xylanolytic or pectinolytic activities such as xylanase, arabinanase, rhamnogalacturonase, pectin acetylesterase, galactanase, polygalacturonase, pectin lyase, pectate lyase, endo-glucanase or pectin methylesterase. The additional enzyme(s) may be producible by means of a microorganism belonging to the genus Aspergillus, preferably *aspergillus niger, Aspergillus aculeatus, Aspergillus awamoi* or *Aspergillus oryzae*.

Test Methods:

Standard incubations: For characterization of enzymes, incubations are carried out in Eppendorf tubes comprising 1 ml of substrate (AZCL-xyloglucan substrates or pure polysaccharides from MegaZyme, Australia). 0.5 ml 0.4% AZCL-substrate suspension is mixed with 0.5 ml 0.1M citrate/phosphate buffer of optimal pH and 10 μl of a suitably diluted enzyme solution is added. Incubations are carried out in Eppendorf Theromixers for 15 minutes at 30° C. (if not otherwise specified) before heat-inactivation for 20 minutes at 95° C. Enzyme incubations are carried out in triplicate. A blank is produced in which enzyme is added but inactivated immediately. After centrifugation the absorbance of the supernatant is measured in microtiter plates at 620 nm and the blank is subtracted.

The activities of the enzymes are measured on different pure polysaccharides: xyloglucan and β-glucan from Mega-Zyme (AZCL-xyloglucan and AZCL-HE cellulose), CMC (Blanose from Aqualon) and Avicell (microcrystaline cellulose from Merck). Before use, Avicell is swelled in 85% orthophosphoric acid for 1 hour at room temperature and washed with acetone and water. 0.5% solutions/suspensions of the different substrates are made in 0.1M acetate buffer (if not otherwise specified) of the optimal pH, 10 µl enzyme solutions are added to 1 ml of substrate, incubations are carried at 30° C. for 15 minutes before heat-inactivation as above. Reducing sugars are determined by reaction, in microtiter plates, with a PHBAH reagent comprising 0.15 g of para hydroxy benzoic acid hydrazide (Sigma H-9882), 0.50 g of potassium-sodium tartrate (Merck 8087) and 2% NaOH solution up to 10.0 ml. Results of blanks are subtracted. Glucose is used as a standard.

pH optimum is measured on substrates from MegaZyme (for the enzymes described hereinafter: EG II on AZCL-xylogulcan, EG III on pure β-glucan, and EG IV on AZCL-β-glucan). 0.5 ml of 0.4% substrate is mixed with 0.5 ml 0.1M citrate/phosphate buffer of varying pH and 10 µl of a suitably diluted enzyme solution is added. Incubations are carried out as described above. While enzymes useful herein may have optimum pH at any pH as desired to match the pH of the composition or cleaning method in which it will be used, preferably the enzymes useful herein are active within the pH range of from about pH 6–11, preferably 7–11, and more preferably within from about 8 to about 10.5.

The specificity of the different enzymes on the different AZCL-substrates is tested as above at optimal pH in 0.1M acetate buffer. pH stability is measured by leaving the enzyme for 1 hour in 0.1M citric acid/tri sodium phosphate buffers of varying pH before the enzyme is used for incubation of AZCL-β-glucan at the optimal pH.

Temperature optimum is measured by incubating the enzyme with AZCL-β-glucan substrate at varying temperatures for 15 minutes at the optimal pH.

Temperature stability is measured by leaving the enzyme, diluted in water, at various temperatures for 1 hour before incubation at 30° C. with the relevant substrate.

Km and specific activity are measured by carrying out incubations at substrate concentrations (S) ranging from 0.025 to 1.5% (hereinafter: xyloglucan for EG II and β-glucan for EG IV), measure the reaction rate (v), picture S/v as a function of S, carry out linear regression analysis, finding the slope (=1/Vmax) and the intercept (Km/Vmax) and calculating Km and the specific activity (=Vmax/E), where E is the amount of enzyme added.

For gel filtration chromatography, 1% solutions/suspensions of the above mentioned pure polysaccharides are made. A suitable amount of enzyme is added and incubations are carried out for 0, 1, 2, 4 and 24 hours before heat-inactivation. 25 µl of sample is injected into three TSK-columns in a row (PW G4000, PW G3000, PW G2500) and saccharides are eluted with 0.4M acetate buffer pH 3.0 at 0.8 ml/min. Eluting saccharides are determined by a Shimadzu RI detector and data are collected and processed by Dionex software. Dextrans (from Sersa) are used as molecular weight standards.

Substrate specificity

The relative activity determined as the release of reducing sugar of different enzymes from different polysaccharides compared to the optimal substrate (100%) is provided in WO 94/14953 and reproduced in the table below.

| Enzyme | EG II | EG III | EG IV |
|---|---|---|---|
| Avicell | 1% | 0% | 3% |
| CMC | 1% | 2% | 11% |
| β-glucan | 0% | 100% | 100% |
| xyloglucan | 100% | 31% | 0% |

From these results the specificities of the different endo-glucanases are presented as:

| Enzyme | EG II | EG III | EG IV |
|---|---|---|---|
| XGU/BGU | ∞ | 0.31 | 0 |
| XGU/CMC | 104 | 18 | 0 |
| XGU/AVIU | 114 | ∞ | 0 |
| BGU/XGU | 0 | 3.2 | ∞ |
| BGU/CMC | 0 | 58 | 9.4 |
| BGU/AVIU | 0 | ∞ | 25 |

The results of substrate specificity determined on AZCL-substrates is also provided in WO 94/14953, and reproduced in the following table:

| Enzyme | EG II | EG III | EG IV |
|---|---|---|---|
| HE-cellulose | 1% | 100% | 100% |
| β-glucan | 0% | 36% | 56% |
| Xyloglucan | 100% | 33% | 1% |
| Curdlan | 0% | 2% | 4% |

From the specificity results it is seen that compared to EG III and EG IV, EG II is specific for xyloglucan, as defined herein for use in the present invention compositions whereas the other two endoglucanases are not. EG III is active towards all types of substrates, but does not have its highest activity for xyloglucan, whereas EG IV cannot degrade xyloglucan and is very specific for β-glucans. (There are some differences in the results obtained with reducing sugars and AZCL-substrates. An explanation for this is that some AZCL-substrates are more sensitive than others. In this case AZCL-HE-cellulose seems to be more sensitive than AZCL-β-glucan).

The Km and specific activity for EG II and EG III are provided in WO 94/14953. The standard deviations on 1/Vmax and Km/Vmax obtained from the linear regression analysis were used therein to calculate the intervals for the enzymes apparent from the following table:

| Enzyme | Substrate | Km % Substrate | Spec. act units/mg | r^2 |
|---|---|---|---|---|
| EG II | xyloglucan | 0.242–0.306 | 106–119 | 0.98 |
| EG III | β-glucan | 0.136–0.207 | 165–186 | 0.98 |

Temperature optimum and temperature/pH stability - EG II and EG III have similar temperature optimums (optimal activity between 30° C. and 60° C.) and temperature stability (stable for 1 h up to 60° C.) but EG III is more stable at alkaline pH than EG II.

The gelfiltration chromatograms, which verify the substrate specificities, show that EG II degrades xyloglucan completely into oligomers of approximately 7–9 residues which are the known repeating subunits of xyloglucans (Fry, 1989). EG III degrades xyloglucan to a much lesser extent and EG IV does not degrade xyloglucan at all. EG III degrades β-glucan to a large extent into DP 3–4 and higher oligomers. This is in accordance with β-glucans being composed of 3–4 β-1, 4-linked glucose units in a row interrupted by single β-1, 3-linkages.

Cleaning Composition Ingredients and Detergent Compositions

The detergent compositions of the invention contain laundry or cleaning composition ingredients as described hereinafter. The precise nature of these components, and levels of incorporation thereof will depend on the physical form of the composition, and the nature of the cleaning operation for which it is to be used. The detergent compositions according to the invention can be liquid, paste, gels, bars, tablets, powder or granular forms. Granular compositions can also be in "compact" form, the liquid compositions can also be in a "concentrated" form.

The compositions of the invention may for example, be formulated as hand and machine laundry detergent compositions including laundry additive compositions and compositions suitable for use in the soaking and/or pretreatment of stained fabrics, rinse added fabric softener compositions. Pre-or post treatment of fabric include gel, spray and liquid fabric conditioning compositions.

When formulated as compositions suitable for use in a laundry machine washing method, the compositions of the invention preferably contain both a surfactant and a builder compound and additionally one or more detergent components preferably selected from organic polymeric compounds, bleaching agents, additional enzymes, suds suppressors, dispersants, lime-soap dispersants, soil suspension and anti-redeposition agents and corrosion inhibitors. Laundry compositions can also contain softening agents, as additional detergent components.

The compositions of the invention can also be used as detergent additive products. Such additive products are intended to supplement or boost the performance of conventional detergent compositions.

If needed the density of the laundry detergent compositions herein ranges from 400 to 1200 g/liter, preferably 600 to 950 g/liter of composition measured at 20° C.

The "compact" form of the compositions herein is best reflected by density and, in terms of composition, by the amount of inorganic filler salt; inorganic filler salts are conventional ingredients of detergent compositions in powder form; in conventional detergent compositions, the filler salts are present in substantial amounts, typically 17–35% by weight of the total composition.

In the compact compositions, the filler salt is present in amounts not exceeding 15% of the total composition, preferably not exceeding 10%, most preferably not exceeding 5% by weight of the composition.

The inorganic filler salts, such as meant in the present compositions are selected from the alkali and alkaline-earth-metal salts of sulphates and chlorides.

A preferred filler salt is sodium sulphate.

Liquid detergent compositions according to the present invention can also be in a "concentrated form", in such case, the liquid detergent compositions according the present invention will contain a lower amount of water, compared to conventional liquid detergents.

Typically the water content of the concentrated liquid detergent is preferably less than 40%, more preferably less than 30%, most preferably less than 20% by weight of the detergent composition.

Surfactants

Preferably, the detergent compositions according to the present invention comprise a surfactant or surfactant system wherein the surfactant can be selected from nonionic and/or anionic and/or cationic and/or ampholytic and/or zwitterionic and/or semi-polar nonionic surfactants.

The surfactant is typically present at a level of from 0.1% to 60% by weight. More preferred levels of incorporation are 1% to 35% by weight, most preferably from 1% to 30% by weight of detergent compositions in accord with the invention.

The surfactant is preferably formulated to be compatible with enzyme components present in the composition. In liquid or gel compositions the surfactant is most preferably formulated such that it promotes, or at least does not degrade, the stability of any enzyme in these compositions.

Examples of suitable nonionic, anionic, cationic, ampholytic, zwitterionic and semi-polar nonionic surfactants are disclosed in U.S. Pat. Nos. 5,707,950 and 5,576,282.

Highly preferred nonionic surfactants are polyhydroxy fatty acid amide surfactants of the formula:

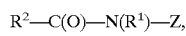

$$R^2-C(O)-N(R^1)-Z,$$

wherein $R^1$ is H, or $R^1$ is $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof Preferably, $R^1$ is methyl, $R^2$ is a straight $C_{11-15}$ alkyl or $C_{16-18}$ alkyl or alkenyl chain such as coconut alkyl or mixtures thereof, and Z is derived from a reducing sugar such as glucose, fructose, maltose, lactose, in a reductive amination reaction.

Highly preferred anionic surfactants include alkyl alkoxylated sulfate surfactants hereof are water soluble salts or acids of the formula $RO(A)_mSO3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein.

When included therein, the laundry detergent compositions of the present invention typically comprise from about 1% to about 40%, preferably from about 3% to about 20% by weight of such anionic surfactants.

Highly preferred cationic surfactants are the water-soluble quaternary ammonium compounds useful in the present composition having the formula:

$$R_1R_2R_3R_4N^+X^-$$

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and $-(C_2H_{4O})_xH$ where x has a value from 2 to 5, and X is an anion. Not more than one of $R_2$, $R_3$ or $R_4$ should be benzyl.

When included therein, the detergent compositions of the present invention typically comprise from 0.2% to about 25%, preferably from about 1% to about 8% by weight of such cationic surfactants.

When included therein, the detergent compositions of the present invention typically comprise from 0.2% to about 15%, preferably from about 1% to about 10% by weight of such ampholytic surfactants.

When included therein, the detergent compositions of the present invention typically comprise from 0.2% to about 15%, preferably from about 1% to about 10% by weight of such zwitterionic surfactants.

When included therein, the detergent compositions of the present invention typically comprise from 0.2% to about 15%, preferably from about 1% to about 10% by weight of such semi-polar nonionic surfactants.

The detergent composition of the present invention may further comprise a co-surfactant selected from the group of primary or tertiary amines.

Suitable primary amines for use herein include amines according to the formula $R_1NH_2$ wherein $R_1$ is a $C_6$–$C_{12}$, preferably $C_6$–$C_{10}$ alkyl chain or $R_4X(CH_2)_n$, X is —O—, —C(O)NH— or —NH—, $R_4$ is a $C_6$–$C_{12}$ alkyl chain n is between 1 to 5, preferably 3. $R_1$ alkyl chains may be straight or branched and may be interrupted with up to 12, preferably less than 5 ethylene oxide moieties.

Preferred amines according to the formula herein above are n-alkyl amines. Suitable amines for use herein may be selected from 1-hexylamine, 1-octylamine, 1-decylamine and laurylamine. Other preferred primary amines include C8–C10 oxypropylamine, octyloxypropylamine, 2-ethylhexyl-oxypropylamine, lauryl amido propylamine and amido propylamine.

Suitable tertiary amines for use herein include tertiary amines having the formula $R_1R_2R_3N$ wherein R1 and R2 are $C_1$–$C_8$ alkylchains or

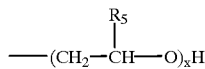

$R_3$ is either a $C_6$–$C_{12}$, preferably $C_6$–$C_{10}$ alkyl chain, or $R_3$ is $R_4X(CH_2)_n$, whereby X is —O—, —C(O)NH— or —NH—, $R_4$ is a $C_4$–$C_{12}$, n is between 1 to 5, preferably 2–3. $R_5$ is H or $C_1$–$C_2$ alkyl and x is between 1 to 6.

$R_3$ and $R_4$ may be linear or branched; $R_3$ alkyl chains may be interrupted with up to 12, preferably less than 5, ethylene oxide moieties.

Preferred tertiary amines are $R_1R_2R_3N$ where R1 is a C6–C12 alkyl chain, R2 and R3 are C1–C3 alkyl or

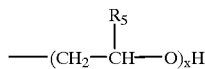

where R5 is H or CH3 and x=1–2.

Also preferred are the amidoamines of the formula:

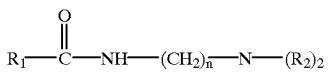

wherein $R_1$ is $C_6$–$C_{12}$ alkyl; n is 2–4, preferably n is 3; $R_2$ and $R_3$ is $C_1$–$C_4$ Most preferred amines of the present invention include 1-octylamine, 1-hexylamine, 1-decylamine, 1-dodecylamine, C8–10oxypropylamine, N coco 1-3diaminopropane, coconutalkyldimethylamine, lauryldimethylamine, lauryl bis(hydroxyethyl)amine, coco bis(hydroxyehtyl)amine, lauryl amine 2 moles propoxylated, octyl amine 2 moles propoxylated, lauryl amidopropyldimethylamine, C8–10 amidopropyldimethylamine and C10 amidopropyldimethylamine.

The most preferred amines for use in the compositions herein are 1-hexylamine, 1-octylamine, 1-decylamine, 1-dodecylaamine. Especially desirable are n-dodecyldimethylamine and bishydroxyethylcoconutalkylamine and oleylamine 7 times ethoxylated, lauryl amido propylamine and cocoamido propylamine.

The surfactant and surfactant system of the present invention is preferably formulated to be compatible with enzyme components present in the composition. In liquid or gel compositions the surfactant is most preferably formulated such that it promotes, or at least does not degrade, the stability of any enzyme in these compositions.

Builders

The compositions according to the present invention may further comprise a builder or builder system. Any conventional builder system is suitable for use herein including aluminosilicate materials, silicates, polycarboxylates, alkyl- or alkenyl-succinic acid and fatty acids, materials such as ethylenediamine tetraacetate, diethylene triamine pentamethyleneacetate, metal ion sequestrants such as aminopolyphosphonates, particularly ethylenediamine tetramethylene phosphonic acid and diethylene triamine pentamethylenephosphonic acid. Phosphate builders can also be used herein.

The present invention may include a suitable builder or detergency salt. The level of detergent salt/builder can vary widely depending upon the end use of the composition and its desired physical form. When present, the compositions will typically comprise at least about 1% builder and more typically from about 10% to about 80%, even more typically from about 15% to about 50% by weight, of the builder. Lower or higher levels, however, are not meant to be excluded.

Inorganic or P-containing detergent salts include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate salts are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Examples of suitable silicate builders, carbonate salts, aluminosilicate builders, polycarboxylate builders, citrate builders, 3,3-dicarboxy-4-oxa-1,6-hexanedioate builders and related compounds disclosed in U.S. Pat. No. 4,566,984, to Bush, succinic acid builders, phosphorous-based builders and fatty acids, are disclosed in U.S. Pat. Nos. 5,576,282, 5,728,671 and 5,707,950.

Additional suitable builders can be an inorganic ion exchange material, commonly an inorganic hydrated aluminosilicate material, more particularly a hydrated synthetic zeolite such as hydrated zeolite A, X, B, HS or MAP.

Specific polycarboxylates suitable for the present invention are polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenlegenschrift 2,446,686, and 2,446,687 and U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2-ethane tetracarboxylates, 1,1,3,3-propane tetracarboxylates and 1,1,2,3-propane tetracarboxylates. Polycarboxylates containing sulfo substituents include the sulfosuccinate derivatives disclosed in British Patent Nos. 1,398, 421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis, cis, cis-tetracarboxylates, cyclopentadienide pentacarboxylates, 2,3,4,5-tetrahydro-furan -cis, cis, cis-tetracarboxylates, 2,5-tetrahydro-furan -cis - dicarboxylates, 2,2,5,5-tetrahydrofuran - tetracarboxylates, 1,2,3,4,5,6-hexane -hexacar-boxylates and and carboxymethyl derivatives of polyhydric alcohols such as sorbitol, mannitol and xylitol. Aromatic poly-carboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

Preferred builder systems include a mixture of a water-insoluble aluminosilicate builder such as zeolite A, and a watersoluble carboxylate chelating agent such as citric acid. Preferred builder systems for use in liquid detergent compositions of the present invention are soaps and polycarboxylates.

Other suitable water-soluble organic salts are the homo- or co-polymeric acids or their salts, in which the polycarboxylic acid comprises at least two carboxyl radicals separated from each other by not more than two carbon atoms. Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition preferably from 10% to 70% and most usually from 30% to 60% by weight.

Bleaching agent

Additional optional detergent ingredients that can be included in the detergent compositions of the present invention include bleaching agents such as hydrogen peroxide, PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%.

The bleaching agent component for use herein can be any of the bleaching agents useful for detergent compositions including oxygen bleaches as well as others known in the art. The bleaching agent suitable for the present invention can be an activated or non-activated bleaching agent.

Examples of suitable bleaching agents are disclosed in U.S. Pat. Nos. 5,707,950 and 5,576,282.

The hydrogen peroxide releasing agents can be used in combination with, for example, the bleach activators disclosed in U.S. Pat. No. 5,707,950 or Phenolsulfonate ester of N-nonanoyl-6-aminocaproic acid (NACA-OBS, described in WO94/28106), which are perhydrolyzed to form a peracid as the active bleaching species, leading to improved bleaching effect. Also suitable activators are acylated citrate esters.

Useful bleaching agents, including peroxyacids and bleaching systems comprising bleach activators and peroxygen bleaching compounds for use in detergent compositions according to the invention are described in WO95/27772, WO95/27773, WO95/27774, WO95/27775 and U.S. Pat. No. 5,707,950.

Metal-containing catalysts for use in bleach compositions, include cobalt-containing catalysts such as Pentaamine acetate cobalt(III) salts and manganese-containing catalysts such as those described in EPA 549 271; EPA 549 272; EPA 458 397; U.S. Pat. No. 5,246,621; EPA 458 398; U.S. Pat. No. 5,194,416 and U.S. Pat. No. 5,114,611. Bleaching composition comprising a peroxy compound, a manganese-containing bleach catalyst and a chelating agent is described in the patent application No 94870206.3.

Dye transfer inhibition

The detergent compositions of the present invention can also include compounds for inhibiting dye transfer from one fabric to another of solubilized and suspended dyes encountered during fabric laundering and conditioning operations involving colored fabrics.

Polymeric dye transfer inhibiting agents

The detergent compositions according to the present invention can also comprise from 0.001% to 10%, preferably from 0.01% to 2%, more preferably from 0.05% to 1% by weight of polymeric dye transfer inhibiting agents. Said polymeric dye transfer inhibiting agents are normally incorporated into detergent compositions in order to inhibit the transfer of dyes from colored fabrics onto fabrics washed therewith. These polymers have the ability to complex or adsorb the fugitive dyes washed out of dyed fabrics before the dyes have the opportunity to become attached to other articles in the wash.

Especially suitable polymeric dye transfer inhibiting agents are polyamine N-oxide polymers, copolymers of N-vinylpyrrolidone and N-vinylimidazole, polyvinylpyrrolidone polymers, polyvinyloxazolidones and polyvinylimidazoles or mixtures thereof. Examples of such dye transfer inhibiting agents are disclosed in U.S. Pat. Nos. 5,707,950 and 5,707,951.

Additional suitable dye transfer inhibiting agents include, but are not limited to, cross-linked polymers. Cross-linked polymers are polymers whose backbone are interconnected to a certain degree; these links can be of chemical or physical nature, possibly with active groups n the backbone or on branches; cross-linked polymers have been described in the Journal of Polymer Science, volume 22, pages 1035–1039.

In one embodiment, the cross-linked polymers are made in such a way that they form a three-dimensional rigid structure, which can entrap dyes in the pores formed by the three-dimensional structure. In another embodiment, the cross-linked polymers entrap the dyes by swelling.

Such cross-linked polymers are described in the co-pending European patent application 94870213.9

Addition of such polymers also enhances the performance of the enzymes according the invention.

Dispersants

The detergent composition of the present invention can also contain dispersants. Suitable water-soluble organic salts are the homo- or co-polymeric acids or their salts, in which the polycarboxylic acid comprises at least two carboxyl radicals separated from each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 1,000 to 100,000.

Especially, copolymer of acrylate and methylacrylate such as the 480N having a molecular weight of 4000, at a level from 0.5–20% by weight of composition can be added in the detergent compositions of the present invention.

The compositions of the invention may contain a lime soap peptiser compound, which has a lime soap dispersing power (LSDP), as defined hereinafter of no more than 8, preferably no more than 7, most preferably no more than 6. The lime soap peptiser compound is preferably present at a level from 0% to 20% by weight.

A numerical measure of the effectiveness of a lime soap peptiser is given by the lime soap dispersant power (LSDP) which is determined using the lime soap dispersant test as described in an article by H. C. Borghetty and C. A. Bergman, J. Am. Oil. Chem. Soc., volume 27, pages 88–90, (1950). This lime soap dispersion test method is widely used by practitioners in this art field being referred to, for example, in the following review articles; W. N. Linfield, Surfactant science Series, Volume 7, page 3; W. N. Linfield, Tenside surf. det., volume 27, pages 159–163, (1990); and M. K. Nagarajan, W. F. Masler, Cosmetics and Toiletries, volume 104, pages 71–73, (1989). The LSDP is the % weight ratio of dispersing agent to sodium oleate required to disperse the lime soap deposits formed by 0.025 g of sodium oleate in 30 ml of water of 333 ppm $CaCo_3$ (Ca:Mg=3:2) equivalent hardness.

Surfactants having good lime soap peptiser capability will include certain amine oxides, betaines, sulfobetaines, alkyl ethoxysulfates and ethoxylated alcohols.

Exemplary surfactants having a LSDP of no more than 8 for use in accord with the present invention include $C_{16}$–$C_{18}$ dimethyl amine oxide, $C_{12}$–$C_{18}$ alkyl ethoxysulfates with an average degree of ethoxylation of from 1–5, particularly $C_{12}$–$C_{15}$ alkyl ethoxysulfate surfactant with a degree of ethoxylation of amount 3 (LSDP=4), and the $C_{14}$–$C_{15}$ ethoxylated alcohols with an average degree of ethoxylation of either 12 (LSDP=6) or 30, sold under the tradenames Lutensol A012 and Lutensol A030 respectively, by BASF GmbH.

Polymeric lime soap peptisers suitable for use herein are described in the article by M. K. Nagarajan, W. F. Masler, to be found in Cosmetics and Toiletries, volume 104, pages 71–73, (1989).

Hydrophobic bleaches such as 4-[N-octanoyl-6-aminohexanoyl]benzene sulfonate, 4-[N-nonanoyl-6-aminohexanoyl]benzene sulfonate, 4-[N-decanoyl-6-aminohexanoyl]benzene sulfonate and mixtures thereof, and nonanoyloxy benzene sulfonate together with hydrophilic/hydrophobic bleach formulations can also be used as lime soap peptisers compounds.

Examples of other suitable dispersing agents are disclosed in U.S. Pat. Nos. 5,576,282 and 5,728,671.

Conventional detergent enzymes

The detergent compositions can comprise in addition to the hexosaminidase enzyme one or more enzymes which provide cleaning performance and/or fabric care benefits.

Said enzymes include enzymes selected from hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and known amylases, or mixtures thereof.

Examples of suitable enzymes are disclosed in U.S. Pat. Nos. 5,576,282, 5,728,671 and 5,707,950

A preferred combination is a detergent composition having cocktail of conventional applicable enzymes like protease, lipase, cutinase and/or cellulase in conjunction with the hexosaminidase.

Particularly useful proteases are described in PCT publications: WO 95/30010 published Nov. 9, 1995 by The Procter & Gamble Company; WO 95/30011 published Nov. 9, 1995 by The Procter & Gamble Company; and WO 95/29979 published Nov. 9, 1995 by The Procter & Gamble Company.

In addition to the peroxidase enzymes disclosed in U.S. Pat. Nos. 5,576,282, 5,728,671 and 5,707,950, other suitable peroxidase enzymes are disclosed in European Patent application EP No. 96870013.8, filed Feb. 20, 1996. Also suitable is the laccase enzyme.

Preferred enhancers are substituted phenthiazine and phenoxasine 10-Phenothiazinepropionicacid (PPT), 10-ethylphenothiazine-4-carboxylic acid (EPC), 10-phenoxazinepropionic acid (POP) and 10-methylphenoxazine (described in WO 94/12621) and substituted syringates (C3–C5 substituted alkyl syringates) and phenols. Sodium percarbonate or perborate are preferred sources of hydrogen peroxide.

Said peroxidases are normally incorporated in the detergent composition at levels from 0.0001% to 2% of active enzyme by weight of the detergent composition.

Other preferred enzymes that can be included in the detergent compositions of the present invention include lipases. Suitable lipase enzymes for detergent usage include those produced by microorganisms of the Pseudomonas group, such as Pseudomonas stutzeri ATCC 19.154, as disclosed in British Patent 1,372,034. Suitable lipases include those which show a positive immunological cross-reaction with the antibody of the lipase, produced by the microorganism *Pseudomonas fluorescent* IAM 1057. This lipase is available from Amano Pharmaceutical Co. Ltd., Nagoya, Japan, under the trade name Lipase P "Amano," hereinafter referred to as "Amano-P". Other suitable commercial lipases include Amano-CES, lipases ex *Chromobacter viscosum*, e.g. *Chromobacter viscosum* var. *lipolyticum* NRRLB 3673 from Toyo Jozo Co., Tagata, Japan; *Chromobacter viscosum* lipases from U.S. Biochemical Corp., U.S.A. and Disoynth Co., The Netherlands, and lipases ex *Pseudomonas gladioli*. Especially suitable lipases are lipases such as M1 Lipase® and Lipomax® (Gist-Brocades) and Lipolase® and Lipolase Ultra® (Novo) which have found to be very effective when used in combination with the compositions of the present invention.

Also suitable are cutinases [EC 3.1.1.50] which can be considered as a special kind of lipase, namely lipases which do not require interfacial activation. Addition of cutinases to detergent compositions have been described in e.g. WO 88/09367 (Genencor).

The lipases and/or cutinases are normally incorporated in the detergent composition at levels from 0.0001% to 2% of active enzyme by weight of the detergent composition.

Known amylases (α and/or β) can be included for removal of carbohydrate-based stains. WO 94/02597, Novo Nordisk A/S published Feb. 03, 1994, describes cleaning compositions which incorporate mutant amylases. See also WO94/18314, Genencor, published Aug. 18, 1994 and WO95/10603, Novo Nordisk A/S, published Apr. 20, 1995. Other amylases known for use in detergent compositions include both α- and β-amylases. α-Amylases are known in the art and include those disclosed in U.S. Pat. No. 5,003,257; EP 252,666; WO 91/00353; FR 2,676,456; EP 285,123; EP 525,610; EP 368,341; and British Patent Specification No. 1,296,839 (Novo). Other suitable amylase are stability-enhanced amylases including Purafact Ox Am® described in WO 94/18314, published Aug. 18, 1994 and WO96/05295, Genencor, published Feb. 22, 1996 and amylase variants from Novo Nordisk A/S, disclosed in WO 95/10603, published April 95.

Examples of commercial α-amylases products are Termamyl®, Ban®, Fungamyl® and Duramyl®, all available from Novo Nordisk A/S Denmark. WO95/26397 describes other suitable amylases: α-amylases characterised by having a specific activity at least 25% higher than the specific activity of Termamyl® at a temperature range of 25° C. to 55° C. and at a pH value in the range of 8 to 10, measured by the Phadebas® α-amylase activity assay. Other amylolytic enzymes with improved properties with respect to the activity level and the combination of thermostability and a higher activity level are described in WO95/35382.

The above-mentioned enzymes may be of any suitable origin, such as vegetable, animal, bacterial, fungal and yeast origin. Purified or non-purified forms of these enzymes may be used. Also included by definition, are mutants of native enzymes. Mutants can be obtained e.g. by protein and/or genetic engineering, chemical and/or physical modifications of native enzymes. Common practice as well is the expression of the enzyme via host organisms in which the genetic material responsible for the production of the enzyme has been cloned.

Said enzymes are normally incorporated in the detergent composition at levels from 0.0001% to 2% of active enzyme by weight of the detergent composition. The enzymes can be added as separate single ingredients (prills, granulates, stabilized liquids, etc. containing one enzyme ) or as mixtures of two or more enzymes ( e.g. cogranulates).

Other suitable detergent ingredients that can be added are enzyme oxidation scavengers. Examples of such enzyme oxidation scavengers are ethoxylated tetraethylene polyamines.

A range of enzyme materials and means for their incorporation into synthetic detergent compositions is also disclosed in WO 9307263 and WO 9307260 to Genencor International, WO 8908694 to Novo, and U.S. Pat. No. 3,553,139, Jan. 5, 1971 to McCarty et al. Enzymes are further disclosed in U.S. Pat. No. 4,101,457, Place et al, Jul. 18, 1978, and in U.S. Pat. No. 4,507,219, Hughes, Mar. 26, 1985. Enzyme materials useful for liquid detergent formulations, and their incorporation into such formulations, are disclosed in U.S. Pat. No. 4,261,868, Hora et al, Apr. 14, 1981. Enzymes for use in detergents can be stabilized by various techniques. Enzyme stabilisation techniques are disclosed and exemplified in U.S. Pat. No. 3,600,319, Aug. 17, 1971, Gedge et al, EP 199,405 and EP 200,586, Oct. 29, 1986, Venegas. Enzyme stabilisation systems are also described, for example, in U.S. Pat. No. 3,519,570. A useful Bacillus, sp. AC13 giving proteases, xylanases and cellulases, is described in WO 9401532 to Novo.

Chelating Agents

The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Examples of suitable chelating agents are disclosed in U.S. Pat. No. 5,728,671.

The compositions herein may also contain water-soluble methyl glycine diacetic acid (MGDA) salts (or acid form) as a chelant or co-builder useful with, for example, insoluble builders such as zeolites, layered silicates and the like.

If utilized, these chelating agents will generally comprise from about 0.1% to about 15% by weight of the detergent compositions herein. More preferably, if utilized, the chelating agents will comprise from about 0.1% to about 3.0% by weight of such compositions.

Suds suppressor

Another optional ingredient is a suds suppressor, exemplified by silicones, and silica-silicone mixtures. Examples of suitable suds suppressors are disclosed in U.S. Pat. Nos. 5,707,950 and 5,728,671. These suds suppressors are normally employed at levels of from 0.001% to 2% by weight of the composition, preferably from 0.01% to 1% by weight.

Softening agents

Fabric softening agents can also be incorporated into laundry detergent compositions in accordance with the present invention. These agents may be inorganic or organic in type. Inorganic softening agents are exemplified by the smectite clays disclosed in GB-A-1 400 898 and in U.S. Pat. No. 5,019,292. Organic fabric softening agents include the water insoluble tertiary amines as disclosed in GB-A1 514 276 and EP-B0 011 340 and their combination with mono C12–C14 quaternary ammonium salts are disclosed in EP-B-0 026 527 and EP-B-0 026 528 and di-long-chain amides as disclosed in EP-B-0 242 919. Other useful organic ingredients of fabric softening systems include high molecular weight polyethylene oxide materials as disclosed in EP-A-0 299 575 and 0 313 146.

Particularly suitable fabric softening agents are disclosed in U.S. Pat. Nos. 5,707,950 and 5,728,673.

Levels of smectite clay are normally in the range from 2% to 20%, more preferably from 5% to 15% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Typical cationic fabric softening components include the water-insoluble quaternary-ammonium fabric softening actives, the most commonly used having been di-long alkyl chain ammonium chloride or methyl sulfate. Preferred cationic softeners among these include the following:

1) ditallow dimethylammonium chloride (DTDMAC);
2) dihydrogenated tallow dimethylammonium chloride;
3) dihydrogenated tallow dimethylammonium methylsulfate;
4) distearyl dimethylammonium chloride;
5) dioleyl dimethylammonium chloride;
6) dipalmityl hydroxyethyl methylammonium chloride;
7) stearyl benzyl dimethylammonium chloride;
8) tallow trimethylammonium chloride;
9) hydrogenated tallow trimethylammonium chloride;

10) $C_{12-14}$ alkyl hydroxyethyl dimethylammonium chloride;

11) $C_{12-18}$ alkyl dihydroxyethyl methylammonium chloride;

12) di(stearoyloxyethyl) dimethylammonium chloride (DSOEDMAC);

13) di(tallowoyloxyethyl) dimethylammonium chloride;

14) ditallow imidazolinium methylsulfate;

15) 1-(2-tallowylamidoethyl)-2-tallowyl imidazolinium methylsulfate.

Biodegradable quaternary ammonium compounds have been presented as alternatives to the traditionally used di-long alkyl chain ammonium chlorides and methyl sulfates. Such quaternary ammonium compounds contain long chain alk(en)yl groups interrupted by functional groups such as carboxy groups. Said materials and fabric softening compositions containing them are disclosed in numerous publications such as EP-A-0,040,562, and EP-A-0,239,910.

Non-limiting examples of softener-compatible anions for the quaternary ammonium compounds and amine precursors include chloride or methyl sulfate.

Others

Other components used in detergent compositions may be employed, such as soil-suspending agents, soil-release agents, optical brighteners, abrasives, bactericides, tarnish inhibitors, coloring agents, and/or encapsulated or non-encapsulated perfumes, examples of which are disclosed in U.S. Pat. Nos. 5,707,950, 5,576,282 and 5,728,671.

Is is well known in the art that free chlorine in tap water rapidly deactivates the enzymes comprised in detergent compositions. Therefore, using chlorine scavenger such as perborate, ammonium sulfate, sodium sulphite or polyethyleneimine at a level above 0.1% by weight of total composition, in the formulas will provide improved through the wash stability of the detergent enzymes. Compositions comprising chlorine scavenger are described in the European patent application 92870018.6 filed Jan. 31, 1992.

Alkoxylated polycarboxylates such as those prepared from polyacrylates are useful herein to provide additional grease removal performance. Such materials are described in WO 91/08281 and PCT 90/01815 at p. 4 et seq., incorporated herein by reference. Chemically, these materials comprise polyacrylates having one ethoxy side-chain per every 7–8 acrylate units. The side-chains are of the formula —$(CH_2CH_2O)_m(CH_2)_nCH_3$ wherein m is 2–3 and n is 6–12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10%, by weight, of the compositions herein.

Method of washing

The compositions of the invention may be used in essentially any washing or cleaning methods, including soaking methods, pretreatment methods and methods with rinsing steps for which a separate rinse aid composition may be added.

The process described herein comprises contacting fabrics with a laundering solution in the usual manner and exemplified hereunder.

The process of the invention is conveniently carried out in the course of the cleaning process. The method of cleaning is preferably carried out at 5° C. to 95° C., especially between 10° C. and 60° C. The pH of the treatment solution is preferably from 7 to 11.

The following examples are meant to exemplify compositions of the present invention, but are not necessarily meant to limit or otherwise define the scope of the invention. In the detergent compositions, the enzyme levels are expressed by pure enzyme by weight of the total composition and unless otherwise specified, the detergent ingredients are expressed by weight of the total compositions. The abbreviated component identifications herein have the following meanings:

LAS: Sodium linear $C_{12}$ alkyl benzene sulphonate

TAS: Sodium tallow alkyl sulphate

CXYAS: Sodium $C_{1X}$–$C_{1Y}$ alkyl sulfate

25EY: A $C_{12}$–$C_{15}$ predominantly linear primary alcohol condensed with an average of Y moles of ethylene oxide CXYFZ: A $C_{1X}$–$C_{1Y}$ predominantly linear primary alcohol condensed with an average of Z moles of ethylene oxide XYEZS: $C_{1X}$–$C_{1Y}$ sodium alkyl sulfate condensed with an average of Z moles of ethylene oxide per mole QAS: $R_2.N^+(CH_3)_2(C_2H_4OH)$ with $R_2=C_{12}$–$C_{14}$ Soap: Sodium linear alkyl carboxylate derived from a 80/20 mixture of tallow and coconut oils.

Nonionic: $C_{13}$–$C_{15}$ mixed ethoxylated/propoxylated fatty alcohol with an average degree of ethoxylation of 3.8 and an average degree of propoxylation of 4.5 sold under the tradename Plurafac LF404 by BASF Gmbh.

CFAA: $C_{12}$–$C_{14}$ alkyl N-methyl glucamide

TFAA: $C_{16}$–$C_{18}$ alkyl N-methyl glucamide.

TPKFA: C12–C14 topped whole cut fatty acids.

DEQA: Di-(tallow-oxy-ethyl) dimethyl ammonium chloride.

Neodol 45–13: C14–C15 linear primary alcohol ethoxylate, sold by Shell Chemical CO.

Silicate: Amorphous Sodium Silicate ($SiO_2:Na_2O$ ratio= 2.0)

NaSKS-6: Crystalline layered silicate of formula δ-$Na_2Si_2O_5$.

Carbonate: Anhydrous sodium carbonate with a particle size between 200 $\mu$m and 900 $\mu$m.

Bicarbonate: Anhydrous sodium bicarbonate with a particle size between 400 $\mu$m and 1200 $\mu$m.

STPP: Anhydrous sodium tripolyphosphate

MA/AA: Copolymer of 1:4 maleic/acrylic acid, average molecular weight about 70,000–80,000

Zeolite A: Hydrated Sodium Aluminosilicate of formula $Na_{12}(AlO_2SiO_2)_{12}$ 0.27$H_2O$ having a primary particle size in the range from 0.1 to 10 micrometers Citrate: Tri-sodium citrate dihydrate of activity 86,4% with a particle size distribution between 425 $\mu$m and 850 $\mu$m.

Citric: Anhydrous citric acid

PB1: Anhydrous sodium perborate monohydrate bleach, empirical formula $NaBO_2.H_2O_2$ PB4: Anhydrous sodium perborate tetrahydrate Percarbonate: Anhydrous sodium percarbonate bleach of empirical formula $2Na_2CO_3.3H_2O_2$ TAED: Tetraacetyl ethylene diamine.

NOBS: Nonanoyloxybenzene sulfonate in the form of the sodium salt.

Photoactivated Bleach: Sulfonated zinc phtalocyanine encapsulated in dextrin soluble polymer.

Protease: Proteolytic enzyme sold under the tradename Savinase, Alcalase, Durazym by Novo Nordisk A/S, Maxacal, Maxapem sold by Gist-Brocades and proteases described in patents WO91/06637 and/or WO95/ 10591 and/or EP 251 446.

Amylase: Amylolytic enzyme sold under the tradename Purafact Ox Am® described in WO 94/18314, WO96/05295 sold by Genencor; Termarnyl®, Fungamyl® and Duramyl®, all available from Novo Nordisk A/S and those described in WO95/26397.

Lipase: Lipolytic enzyme sold under the tradename Lipolase, Lipolase Ultra by Novo Nordisk A/S Xyloglucanase An endoglucanase specific for xyloglucan as described hereinbefore and in WO 94/14953 as EG II.

Cellulase: Cellulytic enzyme sold under the tradename Carezyme, Celluzyme and/or Endolase by Novo Nordisk A/S.

CMC: Sodium carboxymethyl cellulose.

HEDP: 1,1-hydroxyethane diphosphonic acid.

DETPMP: Diethylene triamine penta (methylene phosphonic acid), marketed by Monsanto under the Trade name Dequest 2060.

PVNO: Poly(4-vinylpyridine)-N-Oxide.

PVPVI: Poly (4-vinylpyridine)-N-oxide/copolymer of vinyl-imidazole and vinyl-pyrrolidone.

Brightener 1: Disodium 4,4'-bis(2-sulphostyryl)biphenyl.

Brightener 2: Disodium 4,4'-bis(4-anilino-6-morpholino-1.3.5-triazin-2-yl) stilbene-2:2'-disulfonate.

Silicone antifoam: Polydimethylsiloxane foam controller with siloxane-oxyalkylene copolymer as dispersing agent with a ratio of said foam controller to said dispersing agent of 10:1 to 100:1.

Granular Suds Suppressor: 12% Silicone/silica, 18% stearyl alcohol, 70% starch in granular form SRP 1: Sulfobenzoyl or sodium isethionate end capped esters with oxyethylene oxy and terephtaloyl backbone.

SRP 2: Diethoxylated poly (1,2 propylene terephtalate) short block polymer.

Sulphate: Anhydrous sodium sulphate.

HMWPEO: High molecular weight polyethylene oxide

EXAMPLE 1

The following detergent formulations, according to the present invention are prepared, where I and III are phosphorus-containing detergent compositions, and II is a zeolite-containing detergent composition:

|  | I | II | III |
|---|---|---|---|
| Blown Powder: | | | |
| STPP | 24.0 | — | 24.0 |
| Zeolite A | — | 24.0 | — |
| C45AS | 9.0 | 6.0 | 13.0 |
| MA/AA | 2.0 | 4.0 | 2.0 |
| LAS | 6.0 | 8.0 | 11.0 |
| TAS | 2.0 | — | — |
| Silicate | 7.0 | 3.0 | 3.0 |
| CMC | 1.0 | 1.0 | 0.5 |
| Brightener 2 | 0.2 | 0.2 | 0.2 |
| Soap | 1.0 | 1.0 | 1.0 |
| DETPMP | 0.4 | 0.4 | 0.2 |
| Spray On | | | |
| C45E7 | 2.5 | 2.5 | 2.0 |
| C25E3 | 2.5 | 2.5 | 2.0 |
| Silicone antifoam | 0.3 | 0.3 | 0.3 |
| Perfume | 0.3 | 0.3 | 0.3 |
| Dry additives: | | | |
| Carbonate | 6.0 | 13.0 | 15.0 |
| PB4 | 18.0 | 18.0 | 10.0 |
| PB1 | 4.0 | 4.0 | 0 |
| TAED | 3.0 | 3.0 | 1.0 |
| Photoactivated bleach | 0.02 | 0.02 | 0.02 |
| Protease | 0.01 | 0.01 | 0.01 |
| Lipase | 0.009 | 0.009 | — |
| Amylase | 0.002 | — | 0.001 |
| Xyloglucanase | 0.05 | 0.05 | 0.05 |
| Dry mixed sodium sulfate | 3.0 | 3.0 | 5.0 |
| Balance (Moisture & Miscellaneous) | 100.0 | 100.0 | 100.0 |
| Density (g/liter) | 630 | 670 | 670 |

EXAMPLE 2

The following nil bleach-containing detergent formulations of particular use in the washing of colored clothing, according to the present invention are prepared:

|  | I | II | III |
|---|---|---|---|
| Blown Powder: | | | |
| Zeolite A | 15.0 | 15.0 | — |
| Sodium sulfate | 0.0 | 5.0 | — |
| LAS | 3.0 | 3.0 | — |
| DETPMP | 0.4 | 0.5 | — |
| CMC | 0.4 | 0.4 | — |
| MA/AA | 4.0 | 4.0 | — |
| Agglomerates | | | |
| C45AS | — | — | 11.0 |
| LAS | 6.0 | 5.0 | — |
| TAS | 3.0 | 2.0 | — |
| Silicate | 4.0 | 4.0 | — |
| Zeolite A | 10.0 | 15.0 | 13.0 |
| CMC | — | — | 0.5 |
| MA/AA | — | — | 2.0 |
| Carbonate | 9.0 | 7.0 | 7.0 |
| Spray On | | | |
| Perfume | 0.3 | 0.3 | 0.5 |
| C45E7 | 4.0 | 4.0 | 4.0 |
| C25E3 | 2.0 | 2.0 | 2.0 |
| Dry additives | | | |
| MA/AA | — | — | 3.0 |
| NaSKS-6 | — | — | 12.0 |
| Citrate | 10.0 | — | 8.0 |
| Bicarbonate | 7.0 | 3.0 | 5.0 |
| Carbonate | 8.0 | 5.0 | 7.0 |
| PVPVI/PVNO | 0.5 | 0.5 | 0.5 |
| Protease | 0.026 | 0.016 | 0.047 |
| Lipase | 0.009 | — | 0.009 |
| Amylase | 0.005 | 0.005 | — |
| Xyloglucanase | 0.05 | 0.05 | 0.05 |
| Cellulase | 0.006 | 0.006 | — |
| Silicone antifoam | 5.0 | 5.0 | 5.0 |
| Dry additives | | | |
| Sodium sulfate | 0.0 | 9.0 | 0.0 |
| Balance (Moisture and Miscellaneous) | 100.0 | 100.0 | 100.0 |
| Density (g/liter) | 700 | 700 | 700 |

EXAMPLE 3

The following detergent formulations, according to the present invention are prepared:

|                | I    | II   | III  | IV   |
|----------------|------|------|------|------|
| LAS            | 20.0 | 14.0 | 24.0 | 22.0 |
| QAS            | 0.7  | 1.0  | —    | 0.7  |
| TFAA           | —    | 1.0  | —    | —    |
| C25E5/C45E7    | —    | 2.0  | —    | 0.5  |
| C45E3S         | —    | 2.5  | —    | —    |
| STPP           | 30.0 | 18.0 | 30.0 | 22.0 |
| Silicate       | 9.0  | 5.0  | 10.0 | 8.0  |
| Carbonate      | 13.0 | 7.5  | —    | 5.0  |
| Bicarbonate    | —    | 7.5  | —    | —    |
| DETPMP         | 0.7  | 1.0  | —    | —    |
| SRP 1          | 0.3  | 0.2  | —    | 0.1  |
| MA/AA          | 2.0  | 1.5  | 2.0  | 1.0  |
| CMC            | 0.8  | 0.4  | 0.4  | 0.2  |
| Xyloglucanase  | 0.05 | 0.05 | 0.05 | 0.05 |
| Protease       | 0.008 | 0.01 | 0.026 | 0.026 |
| Amylase        | 0.007 | —    | 0.005 | 0.002 |
| Lipase         | 0.004 | —    | —    | 0.002 |
| Cellulase      | 0.0015 | 0.0005 | — | — |
| Photoactivated bleach | 70 ppm | 45 ppm | — | 10 ppm |
| Brightener 1   | 0.2  | 0.2  | 0.08 | 0.2  |
| PB1            | 6.0  | 2.0  | —    | —    |
| NOBS           | 2.0  | 1.0  | —    | —    |
| Balance (Moisture and Miscellaneous) | 100 | 100 | 100 | 100 |

EXAMPLE 4

The following liquid detergent formulations, according to the present invention are prepared:

|                       | I    | II   | III  | IV   | V    | VI   | VII  | VIII |
|-----------------------|------|------|------|------|------|------|------|------|
| LAS                   | 10.0 | 13.0 | 9.0  | —    | 25.0 | —    | —    | —    |
| C25AS                 | 4.0  | 1.0  | 2.0  | 10.0 | —    | 13.0 | 18.0 | 15.0 |
| C25E3S                | 1.0  | —    | —    | 3.0  | —    | 2.0  | 2.0  | 4.0  |
| C25E7                 | 6.0  | 8.0  | 13.0 | 2.5  | —    | —    | 4.0  | 4.0  |
| TFAA                  | —    | —    | —    | 4.5  | —    | 6.0  | 8.0  | 8.0  |
| QAS                   | —    | —    | —    | —    | 3.0  | 1.0  | —    | —    |
| TPKFA                 | 2.0  | —    | 13.0 | 2.0  | —    | 15.0 | 7.0  | 7.0  |
| Rapeseed fatty acids  | —    | —    | —    | 5.0  | —    | —    | 4.0  | 4.0  |
| Citric                | 2.0  | 3.0  | 1.0  | 1.5  | 1.0  | 1.0  | 1.0  | 1.0  |
| Dodecenyl/tetradecenyl succinic acid | 12.0 | 10.0 | — | — | 15.0 | — | — | — |
| Oleic acid            | 4.0  | 2.0  | 1.0  | —    | 1.0  | —    | —    | —    |
| Ethanol               | 4.0  | 4.0  | 4.0  | 7.0  | 2.0  | 7.0  | 3.0  | 2.0  |
| 1,2 Propanediol       | 4.0  | 4.0  | 2.0  | 7.0  | 6.0  | 8.0  | 10.0 | 13.- |
| Mono Ethanol Amine    | —    | —    | —    | 5.0  | —    | —    | 9.0  | 9.0  |
| Tri Ethanol Amine     | —    | —    | 8    | —    | —    | —    | —    | —    |
| NaOH (pH)             | 8.0  | 8.0  | 7.6  | 7.7  | 8.0  | 7.5  | 8.0  | 8.2  |
| Ethoxylated tetraethylene pentamine | 0.5 | — | 0.5 | 0.2 | — | — | 0.4 | 0.3 |
| DETPMP                | 1.0  | 1.0  | 0.5  | 1.0  | 2.0  | 1.2  | 1.0  | —    |
| SRP 2                 | 0.3  | —    | 0.3  | 0.1  | —    | —    | 0.2  | 0.1  |
| PVNO                  | —    | —    | —    | —    | —    | —    | —    | 0.10 |
| Xyloglucanase         | 0.05 | 0.05 | 0.05 | 0.05 | 0.05 | 0.05 | 0.05 | 0.05 |
| Protease              | .005 | .005 | .004 | .003 | 0.08 | .005 | .003 | .006 |
| Lipase                | —    | .002 | —    | .0002 | —   | —    | .003 | .003 |
| Amylase               | .002 | —    | —    | .004 | .002 | .008 | .005 | .005 |
| Cellulase             | —    | —    | —    | .0001 | —   | —    | .0004 | .0004 |
| Boric acid            | 0.1  | 0.2  | —    | 2.0  | 1.0  | 1.5  | 2.5  | 2.5  |
| Na formate            | —    | —    | 1.0  | —    | —    | —    | —    | —    |
| Ca chloride           | —    | 0.015 | —   | 0.01 | —    | —    | —    | —    |
| Bentonite clay        | —    | —    | —    | —    | —    | 4.0  | 4.0  | —    |
| Suspending clay SD3   | —    | —    | —    | —    | —    | 0.6  | 0.3  | —    |
| Balance Moisture and Miscellaneous | 100 | 100 | 100 | 100 | 100 | 100 | 100 | 100 |

EXAMPLE 5

Granular fabric detergent compositions which provide "softening through the wash" capability are prepared in accord with the present invention:

|  | I | II |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| PB1 | 15.0 | — |
| Percarbonate | — | 15.0 |
| TAED | 5.0 | 5.0 |
| Smectite clay | 10.0 | 5.0 |
| HMWPEO | — | 0.1 |
| Xyloglucanase | 0.05 | 0.05 |
| Protease | 0.02 | 0.01 |
| Lipase | 0.02 | 0.01 |
| Amylase | 0.01 | 0.005 |
| Cellulase | 0.001 | — |
| Silicate | 3.0 | 5.0 |
| Carbonate | 10.0 | 10.0 |
| Granular suds suppressor | 1.0 | 4.0 |
| CMC | 0.2 | 0.1 |
| Water/minors | Up to 100% | |

EXAMPLE 6

Syndet bar fabric detergent compositions are prepared in accord with the present invention:

|  | I | II | III | IV |
|---|---|---|---|---|
| C26 AS | 20.00 | 20.00 | 20.00 | 20.00 |
| CFAA | 5.0 | 5.0 | 5.0 | 5.0 |
| LAS (C11–13) | 10.0 | 10.0 | 10.0 | 10.0 |
| Sodium carbonate | 25.0 | 25.0 | 25.0 | 25.0 |
| Sodium pyrophosphate | 7.0 | 7.0 | 7.0 | 7.0 |
| STPP | 7.0 | 7.0 | 7.0 | 7.0 |
| Zeolite A | 5.0 | 5.0 | 5.0 | 5.0 |
| CMC | 0.2 | 0.2 | 0.2 | 0.2 |
| Polyacrylate (MW 1400) | 0.2 | 0.2 | 0.2 | 0.2 |
| Coconut monethanolamide | 5.0 | 5.0 | 5.0 | 5.0 |
| Xyglucanase | 0.05 | 0.05 | 0.05 | 0.05 |
| Amylase | 0.01 | — | 0.005 | — |
| Protease | 0.3 | — | 0.5 | 0.05 |
| Brightener, perfume | 0.2 | 0.2 | 0.2 | 0.2 |
| CaSO4 | 1.0 | 1.0 | 1.0 | 1.0 |
| MgSO4 | 1.0 | 1.0 | 1.0 | 1.0 |
| Water | 4.0 | 4.0 | 4.0 | 4.0 |
| Filler*: balance to 100% | | | | |

*Can be selected from convenient materials such as CaCO3, talc, clay (Kaolinite, Smectite), silicates, and the like.

---

What is claimed is:

1. A laundry or cleaning product comprising one or more enzymes exhibiting its highest endoglucanse activity on a xyloglucan substrate and one or more surfactants wherein said enzyme exhibiting it highest endoglucanse activity on a xyloglucan substrate is selected from an enzyme which:

i) is encoded by a DNA sequence comprising or included in at least one of the following partial sequences:

(a) ATTCATTTGT GGACAGTGGA C (SEQ ID No: 1)

(b) GTTGATCGCA CATTGAACCA (SEQ ID NO: 2)

(c) ACCCCAGCCG ACCGATTGTC (SEQ ID NO: 3)

(d) CTTCCTTACC TCACCATCAT (SEQ ID NO: 4)

(e) TTAACATCTT TTCACCATGA (SEQ ID NO: 5)

(f) AGCTTTCCCT TGTGTGGGTT (SEQ ID NO: 6)

(g) GCCACCCTGG CTTCCGCTGC CAGCCTCC (SEQ ID NO: 7)

(h) GACAGTAGCA ATCCAGCATT (SEQ ID NO: 8)

(i) AGCATCAGCC GCTTTGTACA (SEQ ID NO: 9)

(j) CCATGAAGTT CACCGTATTG (SEQ ID NO: 10)

(k) GCACTGCTTC TCTCCCAGGT (SEQ ID NO: 11)

(l) GTGGGCGGCC CCTCAGGCAA (SEQ ID NO: 12)

(m) ACGCTCCTCC AATTTTCTCT (SEQ ID NO: 13)

(n) GGCTGGTAG TAATGAGTCT (SEQ ID NO: 14)

(o) GGCGCAGAGT TTGGCCAGGC (SEQ ID NO: 15)

(p) CAACATCCCC GGTGTTCTGG G (SEQ ID NO: 16)

(q) AAAGATTCAT TTGTGGACAG TGGACGTTGA TCGCACATTG

AACCAACCCC AGCCGACCGA TTGTCCTTCC TTACCTCACC

ATCATTTAAC ATCTTTTCAC CATGAAGCTT CCCTTCTCT

CCCTTGCCAC CCTGGCTTCC GCTGCCAGCC TCCAGCGCCG

CACACTTCTG CGGTCAGTGG GATACCGCCA CCGCCGGTGA

CTTCACCCTG TACAACGACC TTTGGGGCGA GACGGCCGGC

ACCGGCTCCC AGTGCACTGG AGTCGACTCC TACAGCGGCG

ACACCATCGC TTGTCACACC AGCAGGTCCT GGTCGGAGTA

GCAGCAGCGT CAAGAGCTAT GCCAACG (SEQ ID NO: 17) or (r) CAGCATCTCC ATTGAGTAAT CACGTTGGTG TTCGGTGGCC

CGCCGTGTTG CGTGGCGGAG GCTGCCGGGA GACGGGTGGG

GATGGTGGTG GGAGAGAATG TAGGGCGCCG TGTTTCAGTC

CCTAGGCAGG ATACCGGAAA ACCGTGTGGT AGGAGGTTTA

TAGGTTTCCA GGAGACGCTG TATAGGGGAT AAATGAGATT

GAATGGTGGC CACACTCAAA CCAACCAGGT CCTGTACATA

CAATGCATAT ACCAATTATA CCTACCAAAA AAAAAAAAAA

AAAAAAAAAA AAAA (SEQ ID NO: 18)

or a sequence homologous thereto encoding a polypeptide specific for xyloglucan with endoglucanse activity, ii) is immunologically reactive with an antibody against a highly purified endoglucanse encoded by the DNA sequence defined in ) and derived from *Aspergillus aculeatus*, CBS 102.43, and is specific for xyloglucan.

2. A laundry or cleaning product according to claim 1 further comprising laundry or cleaning composition ingredients selected from the group consisting of other detersive enzymes, builders, bleaching agents, and mixtures thereof.

3. A laundry or cleaning product according to claim 2, wherein the other detersive enzyme is selected from the group consisting of proteases, amylases, lipases, cellulases, and mixtures thereof.

4. A laundry or cleaning product to claim 2 wherein the builder is selected from the group consisting of zeolite, phosphate, and mixtures thereof.

5. A laundry or cleaning product according to claim 2 wherein the bleaching agent is selected from the group consisting or perborate, percarbonate, and mixtures thereof.

6. A laundry or cleaning product according to claim 1 wherein the surfactant is selected from the group consisting of anionic surfactants, cationic surfactants, nonionic surfactants, and mixtures thereof.

7. A laundry or cleaning product according to claim 6 wherein the anionic surfactants are selected from the group consisting of alkyl sulfate surfactants, linear alkyl benzene sulfonate surfactants and mixtures thereof.

8. A method for laundering fabrics, said method comprising contacting fabrics in need of cleaning with an aqueous solution containing an effective amount of a product according to claim 1 such that the fabrics are cleaned.

9. A method for cleaning dishes and tableware, said method comprising contacting dishes or tableware in need of cleaning with an aqueous solution containing an effective amount of a product according to claim 1 such that the dishes and tableware are cleaned.

10. A method for cleaning dishes and tableware according to claim 9 wherein said method is carried out in an automatic dishwashing machine.

* * * * *

UNITED STATES PATENT AND TRADEMARK OFFICE
CERTIFICATE OF CORRECTION

PATENT NO.    : 6,489,279 B2
DATED         : December 3, 2002
INVENTOR(S)   : Andre Christian Convents et al.

It is certified that error appears in the above-identified patent and that said Letters Patent is hereby corrected as shown below:

<u>Title page,</u>
Item [86], should read
-- [86] PCT Appl. No.:      PCT/US98/09126
         Filed:             May 5, 1998
         PCT Publ. No.:     WO98/50513
         Publ. Date:        Nov. 12, 1998
         Related US Appl. Data:  60/045,826, filed May 5, 1997 --

Signed and Sealed this

Second Day of September, 2003

JAMES E. ROGAN
*Director of the United States Patent and Trademark Office*

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

ATTCATTTGT GGACAGTGGA C      21

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

GTTGATCGCA CATTGAACCA      20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ACCCCAGCCG ACCGATTGTC                                      20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CTTCCTTACC TCACCATCAT                                      20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

TTAACATCTT TTCACCATGA                                      20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AGCTTTCCCT TCTCTCCCTT                                      20

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GCCACCCTGG CTTCCGCTGC CAGCCTCC                              28

(2) INFORMATION FOR SEQ ID NO:8:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GACAGTAGCA ATCCAGCATT                                               20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

AGCATCAGCC GCTTTGTACA                                               20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CCATGAAGTT CACCGTATTG                                               20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GCACTGCTTC TCTCCCAGGT                                               20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GTGGGCGGCC CCTCAGGCAA                                               20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

ACGCTCCTCC AATTTTCTCT                                                   20

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GGCTGGTAG TAATGAGTCT                                                    19

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

GGCGCAGAGT TTGGCCAGGC                                                   20

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CAACATCCCC GGTGTTCTGG G                                                 21

(2) INFORMATION FOR SEQ ID NO:17:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

AAAGATTCAT TGTGGACAG TGGACGTTGA TCGCACATTG AACCAACCCC AGCCGACCGA         60

TTGTCCTTCC TTACCTCACC ATCATTTAAC ATCTTTTCAC CATGAAGCTT TCCCTTCTCT        120

CCCTTGCCAC CCTGGCTTCC GCTGCCAGCC TCCAGCGCCG CACACTTCTG CGGTCAGTGG        180

GATACCGCCA CCGCCGGTGA CTTCACCCTG TACAACGACC TTTGGGGCGA GACGGCCGGC        240

ACCGGCTCCC AGTGCACTGG AGTCGACTCC TACAGCGGCG ACACCATCGC TTGTCACACC        300

AGCAGGTCCT GGTCGGAGTA GCAGCAGCGT CAAGAGCTAT GCCAACG                     347

(2) INFORMATION FOR SEQ ID NO:18:

(i) SEQUENCE CHARACTERISTICS:
    (A) LENGTH: 294 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:18:

CAGCATCTCC ATTGAGTAAT CACGTTGGTG TTCGGTGGCC CGCCGTGTTG CGTGGCGGAG    60

GCTGCCGGGA GACGGGTGGG GATGGTGGTG GGAGAGAATG TAGGGCGCCG TGTTTCAGTC   120

CCTAGGCAGG ATACCGGAAA ACCGTGTGGT AGGAGGTTTA TAGGTTTCCA GGAGACGCTG   180

TATAGGGGAT AAATGAGATT GAATGGTGGC CACACTCAAA CCAACCAGGT CCTGTACATA   240

CAATGCATAT ACCAATTATA CCTACCAAAA AAAAAAAAAA AAAAAAAAAA AAAA         294